United States Patent
Kurosaka

(10) Patent No.: US 8,801,182 B2
(45) Date of Patent: Aug. 12, 2014

(54) OPTICAL COHERENCE TOMOGRAPHY APPARATUS AND METHOD

(75) Inventor: Ryoji Kurosaka, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 205 days.

(21) Appl. No.: 13/483,358

(22) Filed: May 30, 2012

(65) Prior Publication Data

US 2013/0003015 A1 Jan. 3, 2013

(30) Foreign Application Priority Data

Jun. 28, 2011 (JP) ................................. 2011-143085

(51) Int. Cl.
*A61B 3/14* (2006.01)

(52) U.S. Cl.
USPC ........................................................ 351/206

(58) Field of Classification Search
CPC .............. G06F 3/013; G02B 2027/011; G02B 2027/0178; G02B 26/101; G02B 27/01; G02B 27/017; H04N 13/044; H04N 13/0468
USPC .......... 351/206, 201, 246, 205, 200; 356/497, 356/479, 450, 511
See application file for complete search history.

(56) References Cited

U.S. PATENT DOCUMENTS

| | | | |
|---|---|---|---|
| 2009/0091766 A1* | 4/2009 | Hirose | 356/479 |
| 2011/0242487 A1 | 10/2011 | Yuasa et al. | |
| 2011/0267583 A1 | 11/2011 | Hayashi | |
| 2012/0099076 A1 | 4/2012 | Kurosaka | |

FOREIGN PATENT DOCUMENTS

| | | |
|---|---|---|
| JP | 2007-267927 A | 10/2007 |
| WO | 2010/074321 A1 | 7/2010 |
| WO | 2010/079550 A1 | 7/2010 |
| WO | 2011/118826 A1 | 9/2011 |

OTHER PUBLICATIONS

Sep. 28, 2012 European Communication in European Patent Appln. No. 12171579.1.
Christoph K. Hitzenberger, et al., "Dispersion Effects in Partial Coherence Interferometry: Implications for Intraocular Ranging", Journal of Biomedical Optics, vol. 4, No. 1, Jan. 1999, pp. 144-151.
Jul. 15, 2013 Russian Official Action in Russian Patent Appln. No. 2012126955.
Maciej Wojtkowski, et al., "Ultrahigh-resolution, high-speed, Fourier domain optical coherence tomography and methods for dispersion compensation", Optics Express, vol. 12, No. 11, May 31, 2004, pp. 2404-2422.

* cited by examiner

*Primary Examiner* — Hung Dang
(74) *Attorney, Agent, or Firm* — Fitzpatrick, Cella, Harper & Scinto

(57) ABSTRACT

Measuring light with a wide wavelength band is used to provide a tomographic image excellent in vertical resolution. An optical coherence tomography apparatus acquiring a tomographic image of an object to be inspected based on an interference light obtained by causing a return light from a measuring light emitted onto the object to be inspected to interfere with a reference light corresponding to the measuring light, includes: a first dispersion compensation unit having a first dispersion compensation characteristic in a wavelength band of the measuring light; a second dispersion compensation unit provided onto the first dispersion compensation unit and having a second dispersion compensation characteristic in the wavelength band of the measuring light.

9 Claims, 4 Drawing Sheets

OPTICAL COHERENCE TOMOGRAPHY APPARATUS AND METHOD

BACKGROUND OF THE INVENTION

1. Field of the Invention

The present invention relates to an optical coherence tomography apparatus and method, and more particularly to an optical coherence tomography apparatus and method for imaging a cross-section of the eye fundus and skin.

2. Description of the Related Art

Recent years have seen a practical use of an optical coherence tomography (hereinafter referred to as an OCT) apparatus using an optical coherence technique with low coherence light. The OCT apparatus is a useful apparatus in a medical field, especially in an ophthalmic field. The OCT apparatus can provide a tomographic image of an eye fundus retinal portion and is becoming essential to the diagnosis of diseases of an eye fundus portion.

Here, the principle of the OCT will be described in brief. The low coherence light is divided into reference light and measuring light. The measuring light is incident on an object to be inspected and is reflected on a tomographic imaging region. The reflected return light is made to interfere with the reference light. The obtained interference light can be used to acquire a tomographic image of the object to be inspected. The OCT is classified into a TD (Time Domain) system and an FD (Fourier Domain). The FD-OCT system is a method for acquiring a tomographic image by performing Fourier transform on an interference signal obtained from the interference light with respect to frequency. The FD-OCT system is currently a mainstream since the tomographic image can be acquired at higher speeds than by the TD system.

Recent years have witnessed an attempt to increase the resolution in order to improve the quality of the tomographic image to be acquired. The OCT resolution is divided into a vertical resolution which is a resolution of the measuring light along an optical axis; and a lateral resolution which is a resolution in a direction perpendicular to the optical axis. The vertical resolution is important to identify a layer structure for tomographic fundus measurement using the OCT, and the layer thickness is very important to determine eye disease.

The vertical resolution in the OCT is determined primarily by the performance of the light for use in measurement. If the wavelength spectrum of the light is a Gaussian distribution, the vertical resolution is expressed by the following expression (1).

$$l_c = \sqrt{\left(\frac{2\ln(2)}{\pi} \frac{\lambda_0^2}{\Delta\lambda}\right)^2 + (\Delta GDL \cdot \Delta\lambda)^2} \quad \text{(Expression 1)}$$

Here, $l_c$ denotes a vertical resolution expressed as a half-value width of a coherence function; $\lambda_0$ denotes the central wavelength of light; $\Delta\lambda$ denotes the wavelength width of light; and $\Delta GDL$ denotes the difference in the amount of dispersion between the reference optical system and the measurement reference optical system in the OCT. The above expression assumes that the wavelength spectrum is a Gaussian distribution. If light has a spectrum which is not a Gaussian distribution, the vertical resolution is degraded from the above expression. However, the central wavelength $\lambda_0$ and the light wavelength width $\Delta\lambda$ show a similar change, and thus the above expression does not lose generality.

It is understood from expression (1) that the vertical resolution can be increased by:

(1) reducing the light central wavelength;
(2) increasing light wavelength width; and
(3) uniformizing the dispersion between the reference optical system and the measurement optical system in an interferometer.

The ophthalmologic OCT system uses a near-infrared region (with a wavelength of near 850 nm). The available wavelength band has a limit on a low wavelength side because light is absorbed in the retina. Accordingly, it is difficult to increase the vertical resolution by reducing the central wavelength in the wavelength band used by the ophthalmologic OCT system. Further, the wavelength band also has a limit on a long wavelength side because of absorption loss by vitreous body in front of the eye fundus portion and reduction in sensor sensitivity.

Thus, the vertical resolution can be increased by (2) increasing light wavelength width in consideration of the above limits. In fact, with the recent progress in the practical use of broadband low coherence light, a study has been on increased vertical resolution and clinical value by (2) increasing light wavelength width ("Ultrahigh-resolution, high-speed, Fourier domain optical coherence tomography and methods for dispersion compensation", OPTICS EXPRESS Vol. 12, No. 11, 31 May 2004, PP 2404-2422).

Here, the dispersion compensation will be described. The OCT requires the dispersion characteristics of the reference optical path to be matched with those of the measurement optical path. The matching of the dispersion characteristics is referred to as dispersion compensation. FIG. 8 is a schematic graph illustrating two intensity profiles in the depth direction on a reflecting surface by the OCT: one profile with dispersion compensation and one without dispersion compensation. The dotted line indicates a simplified profile without dispersion compensation; and the solid line indicates a simplified profile with dispersion compensation. FIG. 8 indicates that insufficient dispersion compensation reduces the coherence function intensity indicating a resolution in the depth direction and increases the half-value width, whereby the vertical resolution is degraded.

Japanese Patent Application Laid-Open No. 2007-267927 discloses an OCT system using water for dispersion compensation. The OCT system is characterized in that a container filled with a medium with a moisture content of 70% or more is placed on the reference optical path side, and the above medium can suppress the influence of dispersion caused by an object to be measured. Japanese Patent Application Laid-Open No. 2007-267927 further discloses a technique that can deform the container to provide dispersion compensation according to the state of the object to be inspected.

A document "Ultrahigh-resolution, high-speed, Fourier domain optical coherence tomography and methods for dispersion compensation", OPTICS EXPRESS Vol. 12, No. 11, 31 May 2004, PP 2404-2422 discloses a mathematical dispersion compensation unit using an iterative method by Hilbert transform.

In order to increase the vertical resolution using broadband light in the OCT, it is important to perform dispersion compensation over the wavelength band to be used. Unfortunately, the dispersion characteristics of an object to be measured are different for each wavelength, and thus a broader wavelength band makes it difficult to compensate dispersion by a single material, which may suppress the increase in vertical resolution.

A document "Ultrahigh-resolution, high-speed, Fourier domain optical coherence tomography and methods for dispersion compensation", OPTICS EXPRESS Vol. 12, No. 11, 31 May 2004, PP 2404-2422 discloses an OCT configuration using broadband light. A plurality of glass materials is used to perform dispersion compensation. The materials of water and glass have greatly different dispersion characteristics in a long wavelength range (a wavelength band of about 900 nm to 950 nm). Thus, it is difficult to perform dispersion compensation on water over the broadband by the apparatus configuration disclosed in the above document.

The configuration disclosed in Japanese Patent Application Laid-Open No. 2007-267927 is characterized in that the OCT system uses water for dispersion compensation according to the object to be measured. Unfortunately, this configuration has a problem in routine use because the dispersion compensation using water involves management difficulty and quality deterioration.

SUMMARY OF THE INVENTION

In order to solve the above problems, an optical coherence tomography apparatus acquiring a tomographic image of an object to be inspected based on an interference light obtained by causing a return light from a measuring light emitted onto the object to be inspected to interfere with a reference light corresponding to the measuring light, the apparatus comprising: a first dispersion compensation unit having a first dispersion compensation characteristic in a wavelength band of the measuring light; a second dispersion compensation unit provided onto the first dispersion compensation unit and having a second dispersion compensation characteristic in the wavelength band of the measuring light.

The present invention can perform dispersion compensation on reference light through a reference optical system according to dispersion characteristics of various configurations existing in a measurement optical system over a broadband.

Further features of the present invention will become apparent from the following description of exemplary embodiments with reference to the attached drawing.

DESCRIPTION OF THE EMBODIMENTS

Preferred embodiments of the present invention will now be described in detail in accordance with the accompanying drawings.

The embodiments of the present invention will be described in detail with reference to the accompanying drawings.

First Embodiment

Figure 1:
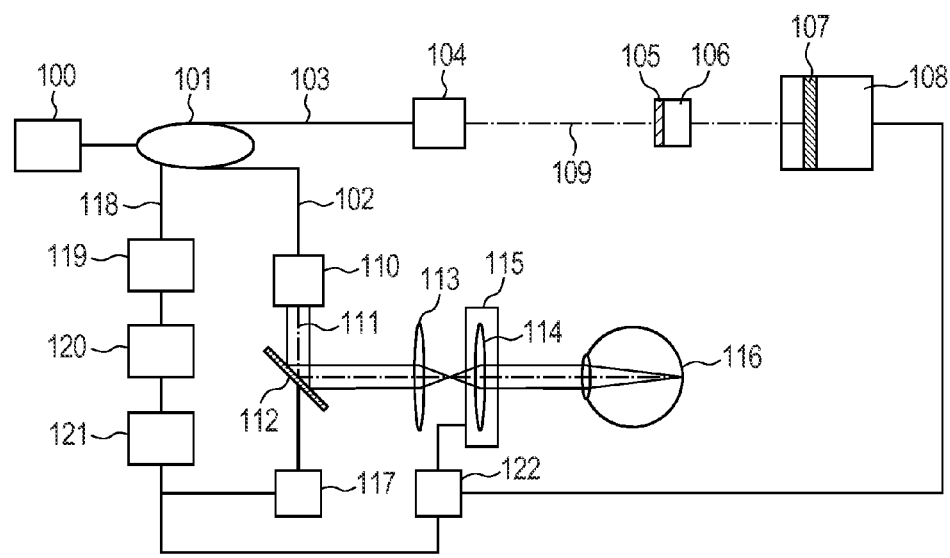
FIG. 1 is a configuration view illustrating a first embodiment.

With reference to FIG. 1, an optical coherence tomography apparatus according to the present invention will be described.

FIG. 1 illustrates the optical coherence tomography apparatus as a specific example for carrying out the present invention.

In FIG. 1, a light source 100 is an SLD (Super Luminescent Diode) in the present embodiment, but may be any low-coherence light source. The specific examples include an ASE (Amplified Spontaneous Emission) light source, an ultrashort pulse light source such as a titanium sapphire laser and an SC (Super Continuum) light source, and an SS (Swept Source) light source. The wavelength band is near 850 nm, but it is desirable that the wavelength band be selected according to the purpose because if a deeper portion of the object to be inspected needs to be measured at the expense of the vertical resolution, a light source having a longer wavelength band is used.

A fiber coupler 101 splits broadband light emitted from the light source 100 into reference light 109 passing through a fiber 103 constituting a reference optical path and measuring light 111 passing through a fiber 102 constituting a measurement optical path. The fiber coupler 101 desirably has a less wavelength dependence on the split ratio of the reference light 109 and the measuring light 111 and has a near constant split ratio. The split measuring light 111 is emitted as collimated light from a fiber collimator 110. The measuring light 111 passing through the fiber collimator 110 into collimated light is emitted to a retina of an eye 116 as the object to be inspected. In order to be scanned on the retina, the measuring light 111 passes through a scanning optical system including a scanner mirror 112 and a scanner lens 113 to be scanned by a scanner mirror controller 117 and then is subjected to focus adjustment by an object lens 114 and an electrically driven stage 115. This focus adjustment is performed by a stage controller 122 connected to a PC 121. Subsequently, the measuring light 111 is reflected by the retina of the eye 116 and proceeds through the above described measurement optical path in the reversed direction.

Meanwhile, the split reference light 109 is emitted as collimated light from the fiber collimator 104, and is incident on a first dispersion compensation member 105 and a second dispersion compensation member 106. The first dispersion compensation member 105 has a first dispersion compensation characteristic, and the second dispersion compensation member 106 has a second dispersion compensation characteristic other than the first dispersion compensation characteristic. According to the present embodiment, the first dispersion compensation member 105 is implemented by BK7 as optical glass, and the second dispersion compensation member 106 is implemented by polycarbonate as optical plastic. For example, BK7 is 23 mm thick, and polycarbonate is about 2 mm thick. The above thickness assumes the 840 nm-thick wavelength band. The above thickness changes depending on the wavelength band. Alternatively, the optical glass 105 may be optical glass other than BK7. For example, F2 may be used. Further, the optical plastic 106 is not limited to polycarbonate. The reference light 109 passing through the dispersion compensation members 105 and 106 is reflected by the reference system reflection mirror 107. The reference system reflection mirror 107 is placed on an electrically driven stage 108 for adjusting positions. Note that the optical path length adjustment of the reference light 109 by the electrically driven stage 108 is controlled by the PC 121 and the stage controller 122.

The measuring light 111 as the return light and the reference light 109 reflected by the reference system reflection mirror 107 are guided by the fiber coupler 101 as interference light onto a spectroscope 119 through a combined optical path fiber 118. The interference light split for each wavelength by the spectroscope 119 is further guided to a light detecting element 120 according to each wavelength. The PC 121 generates a tomographic image from the detection results of the light detecting element 120 using various systems described in the Related Background Art.

According to the present embodiment, the fiber coupler 101 functions as a unit for splitting light emitted from the light source into the reference light 109 and the measuring light 111; and also functions as a unit for obtaining interference light by causing the reflected reference light 109 to interfere with the return light returned from the object to be inspected irradiated with the measuring light 111. The configuration from the spectroscope 119 to the PC 121 corresponds to a unit for acquiring a tomographic image of the object to be inspected based on the interference light.

Now, the dispersion compensation for use in the measurement optical path of the present embodiment will be specifically described. The measurement optical path includes various lenses such as the scanner lens 113 and the object lens 114, and the vitreous body and the crystalline of the lens eye 116 as the object to be inspected, each having a different refractive index for each wavelength. Accordingly, in order to improve the vertical resolution, a member corresponding to each of the above various lenses and the vitreous body and the crystalline lens needs to be inserted into the reference optical path. It is not so difficult to perform dispersion compensation on above various lenses because a lens material may be inserted. However, it is difficult to perform dispersion compensation on the vitreous body and the crystalline lens because the vitreous body and the crystalline lens are mostly water.

Figure 5:
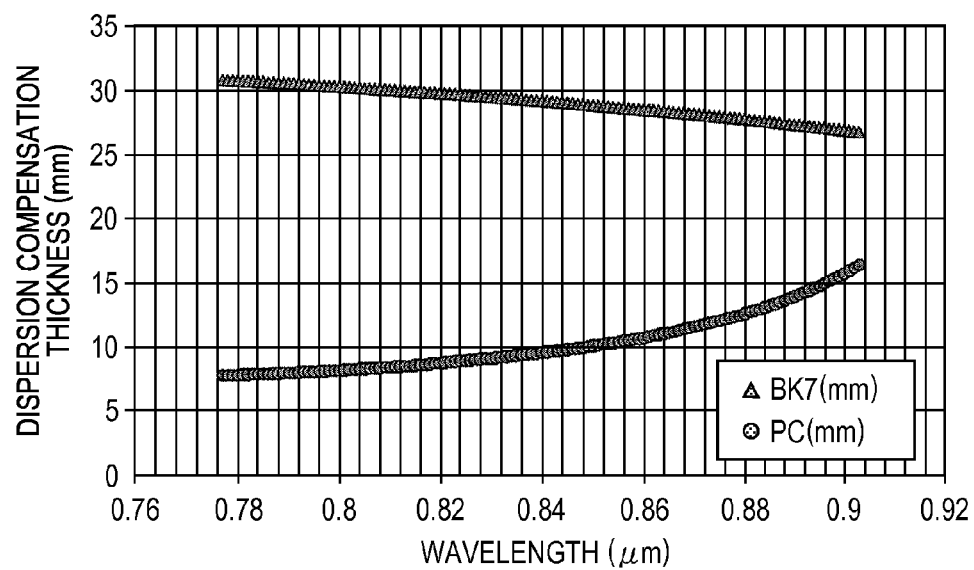
FIG. 5 is a graph of a thickness required for dispersion compensation by each dispersive material.

FIG. 5 illustrates the thickness required for each wavelength of the BK7 and the polycarbonate when used as a single material for dispersion compensation to be performed on an object to be inspected having an average axial length and a dispersive material for use in the measurement optical path illustrated in FIG. 1. It is understood from FIG. 5 that the thickness required for dispersion compensation is greatly different between the short wavelength side and the long wavelength side of the BK7 and the polycarbonate (PC). The reason for this is that the water dispersion characteristics have zero dispersion at about 1 um (μm) of wavelength. Thus, as closed to 1 um, the dispersion characteristics of water as the dispersive material of the eye are greatly different from those of the BK7 and the polycarbonate. As disclosed in JOURNAL OF BIOMEDICAL OPTICS Vol. 4, No. 1, 144-151, the group velocity dispersion GD is expressed as a first derivation about a wavelength of a group refractive index ng by the following expression (2).

$$GD = \frac{dn_g}{d\lambda} = -\lambda \frac{d^2 n}{d\lambda^2} \quad \text{(Expression 2)}$$

Figure 3:
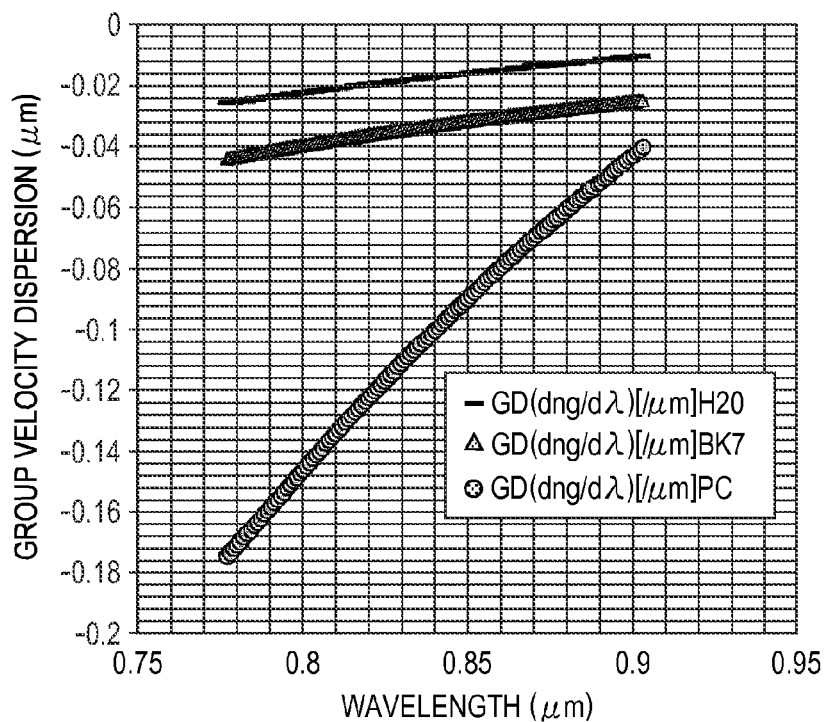
FIG. 3 is a graph of a group velocity dispersion of a dispersive material.
Figure 4:
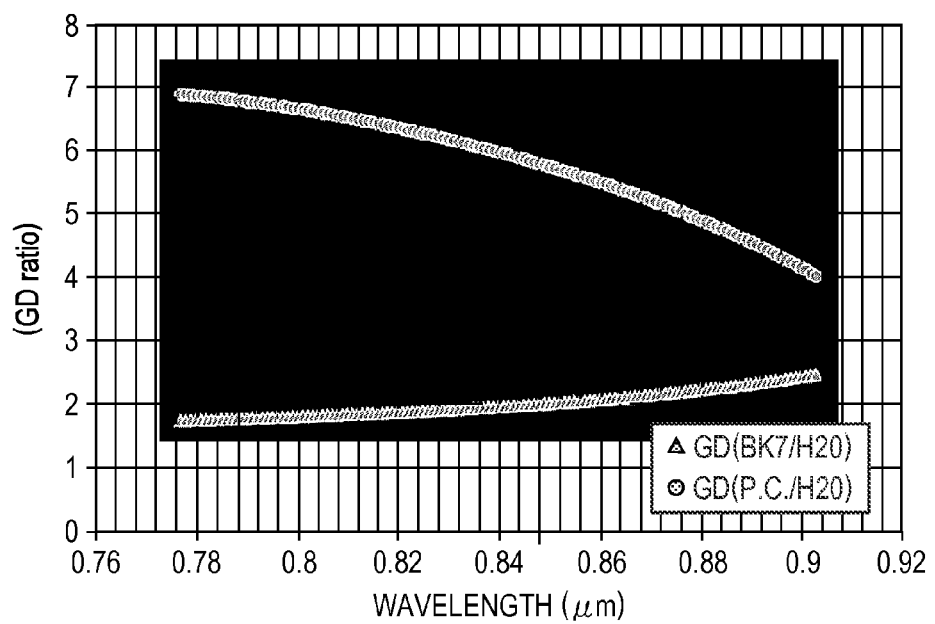
FIG. 4 is a graph of a group velocity dispersion standardized by water.

FIG. 3 is a graph illustrating a wavelength dependence of the group velocity dispersion GD about water as the dispersion compensation member of the dispersion compensation unit and the materials of BK7 and polycarbonate. FIG. 4 is a graph of GD of each dispersion compensation member standardized by GD of water and about the wavelength dependence of expression (3).

$$GD_{ratio} = \frac{GD_{material}}{GD_{water}} \quad \text{(Expression 3)}$$

It is understood that the GD ratio (hereinafter referred to as a GDR) of the BK7 (marked with A in FIG. 4) monotonically increases with respect to the wavelength and the long wavelength side is greater in the group velocity dispersion of the BK7 with respect to water than the short wavelength side. This implies that the thickness required for dispersion compensation is different between the short wavelength side and the long wavelength side when water dispersion compensation is performed by the BK7.

Here, FIG. 5 illustrating the wavelength dependence of the thickness of the BK7 and the polycarbonate required to perform total dispersion on the measurement optical system shows that the dispersion compensation thickness monotonically changes for each wavelength and the closer to the broadband the wavelength of a single use of BK7 or polycarbonate is, the more difficult the dispersion compensation is. Thus, it is concluded from expression (1) that even if the wavelength of the light source is broadband, the OCT vertical resolution cannot afford to complete dispersion compensation, whereby a desired vertical resolution cannot be achieved.

Thus, as illustrated in FIG. 4, the present embodiment uses two kinds of materials in which the GDR wavelength dependence has reverse characteristics. A plurality of dispersion compensation members mathematically expressed as differential characteristics by the follow expression is used.

$$\text{sgn}\left(\frac{d\,GDR_{material1}}{d\lambda}\right) = -\text{sgn}\left(\frac{d\,GDR_{material2}}{d\lambda}\right) \quad \text{(Expression 4)}$$

sgn(x) in expression (4) is a code function, which is 1 if x is positive; 0 if x is 0; and −1 if x is negative. The two kinds of materials: material 1 and material 2 satisfying expression (4) are used and the thickness of both materials is controlled, which can achieve more accurate dispersion compensation than dispersion compensation using a single kind of material. Further, this can perform dispersion compensation on water as a main component of the vitreous body without using water.

For example, in the case of BK7, the differential characteristic about this group velocity dispersion is positive regarding the wavelength of a function expressed by the group velocity dispersion/the group velocity dispersion about a dispersive material of the object to be measured. Thus, the dispersion compensation unit made of a material having differential characteristics such that the sign of the function is reversed to minus is used together with BK7 to cancel the sign, whereby suitable compensation characteristics from the short wavelength side to the long wavelength side can be obtained.

An increase in physical precision of dispersion compensation as described above is expected to lead to reduction in the amount of numerical calculation of dispersion compensation as post processing by an iterative method as disclosed in the document "Ultrahigh-resolution, high-speed, Fourier domain optical coherence tomography and methods for dispersion compensation", OPTICS EXPRESS Vol. 12, No. 11, 31 May 2004, PP 2404-2422, an increase in alignment precision at imaging and reduction in disease imaging missing.

According to the present embodiment, a combination of BK7 and polycarbonate satisfies the relation of expression (4). Note that the present embodiment uses a combination of BK7 and polycarbonate, but any combined materials satisfying the relation of expression (4) may be used. Note also that the materials are not limited to two kinds of materials as long as the materials satisfy the relation of expression (4). For example, three kinds of materials satisfying the relation of expression (5) may be used.

$$\text{sgn}\left(\frac{d\,GDR_{material1}}{d\lambda}\right) = -\text{sgn}\left(\frac{d\,GDR_{material2}}{d\lambda}\right) = -\text{sgn}\left(\frac{d\,GDR_{material3}}{d\lambda}\right) \quad \text{(Expression 5)}$$

Thus, the present embodiment can be defined to have a dispersion compensation unit made of a plurality of dispersion compensation members having different dispersion characteristics. The first embodiment shows a configuration including a first dispersion compensation unit made of a first dispersion compensation member 105 and a second dispersion compensation unit made of a second dispersion compensation member 106. These can be considered to form a part of a configuration including a plurality of dispersion compensation units.

As described above, a plurality of dispersion compensation units preferably includes a pair of dispersion compensation units each made of a set of dispersion compensation members having a relation such that the differential characteristics about the wavelength of the function expressed by the group velocity dispersion of a dispersive material/the group velocity dispersion of the dispersive material of the object to be measured are reversed in sign.

Figure 6:
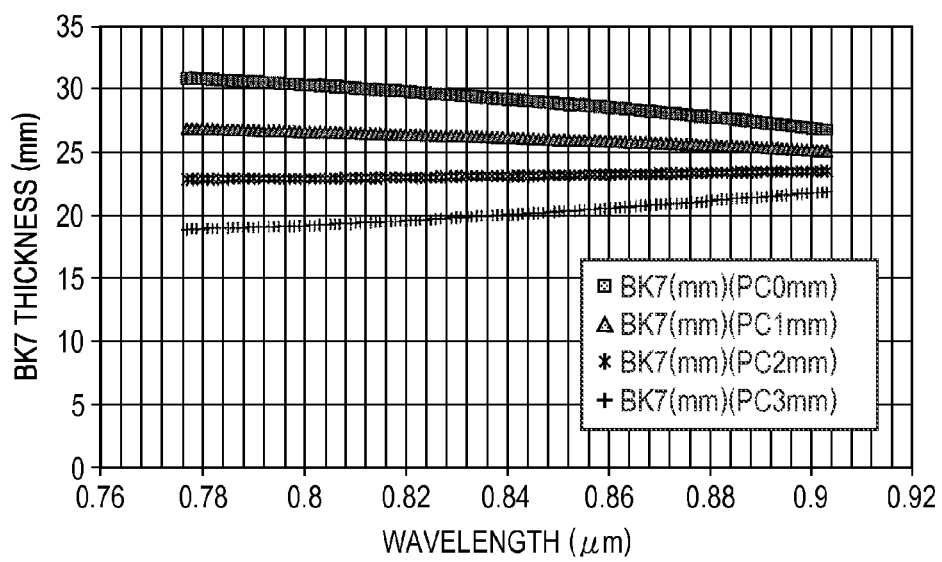
FIG. 6 is a graph of a BK7 thickness taking a polycarbonate thickness of the first embodiment as a parameter.
Figure 7:
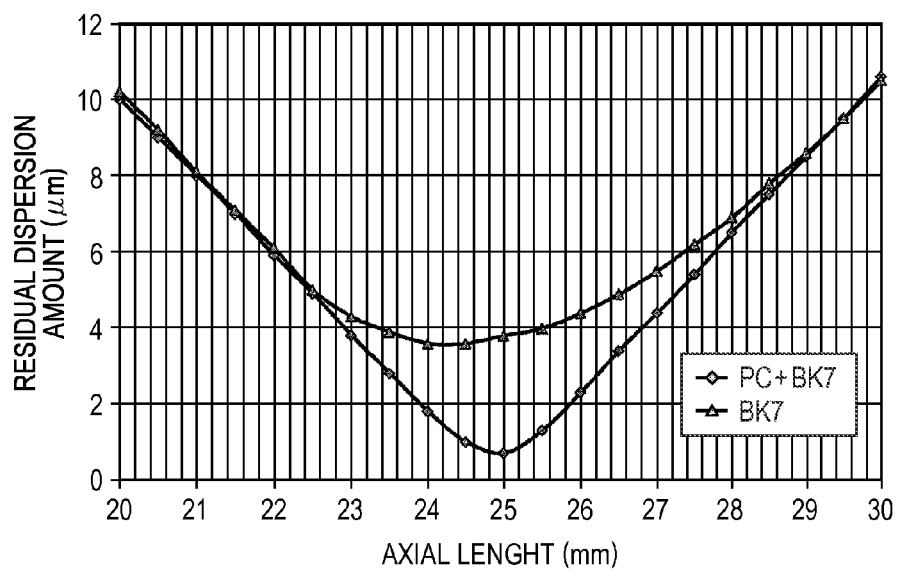
FIG. 7 is a graph about a residual dispersion amount.
Figure 8:
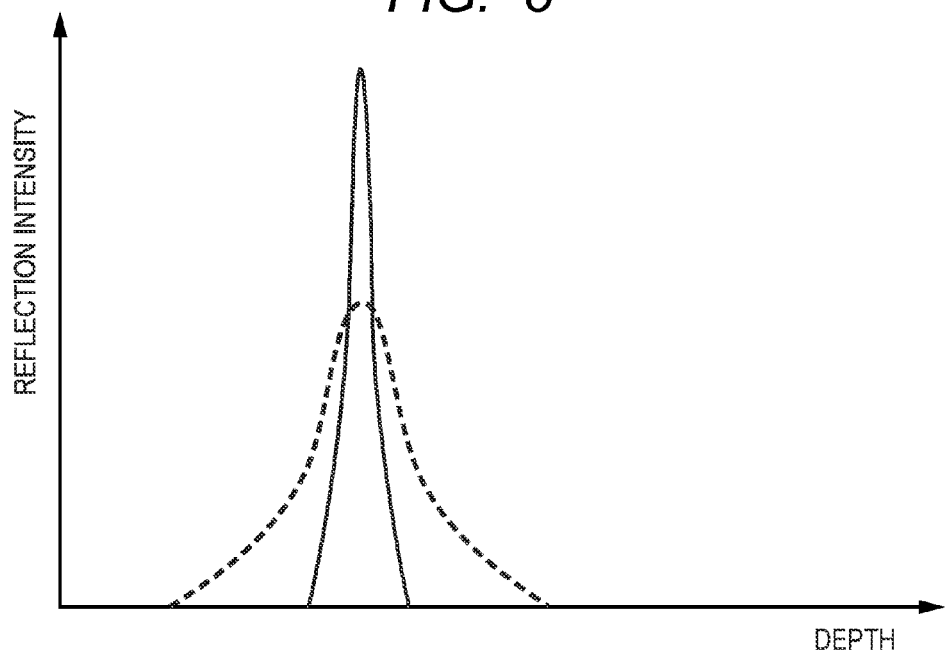
FIG. 8 is a graph about a change in coherence function by dispersion.

FIG. 6 is a graph illustrating a wavelength dependence of the BK7 thickness required for dispersion compensation about total dispersion of the measurement optical system in FIG. 1 when the thickness of the polycarbonate is taken as a parameter. FIG. 6 shows that when the polycarbonate is 2 mm thick, BK7 can perform dispersion compensation at a certain thickness of 23 mm regardless of the wavelength. That is, in the present invention, the BK7 and the polycarbonate have thicknesses without wavelength dependences of the dispersion characteristics over the wavelength band of the measuring light. Specifically, the dispersion compensation characteristics of the BK7 and the polycarbonate in a first or specific wavelength band in the wavelength band of the measuring light are the same as those in a second or wavelength band other than the specific wavelength band in the wavelength band of the measuring light. Note that human eye dispersion is calculated by assuming that the axial length is 25 mm corresponding to 25 mm of water. FIG. 7 is a graph illustrating two residual dispersion amounts: one when only BK7 is used as the dispersion compensation member; and one when BK7 and polycarbonate are used as the dispersion compensation member.

The residual dispersion is the right side term inside the square root in expression (1). The right side term is caused by a difference in dispersion amount between the reference optical system and the measurement optical system in the OCT. The left side term is a full width at half maximum (FWHM) of a coherence function determined by the characteristics of the light source. From expression (1), the right side term inside the square root cannot be ignored from around when the amounts of the left side term and the right side term inside the square root are substantially equal to each other. Assuming that the wavelength width is about 100 nm and the central wavelength is 850 nm, the FWHM of the coherence function of the light source is about 3.2 um in the air equivalent. Even if the non-Gaussian shape of the SLD light source is considered, the FWHM of the coherence function of the light source is about 4 um. From FIG. 7, when dispersion compensation is performed only by BK7, the residual dispersion amount is about 4 um at minimum. This value is about the same as the FWHM of the coherence function of the light source, thereby causing the vertical resolution to be so degraded as not to be ignored. When BK7 and polycarbonate are used, this value is within a sufficiently small range in comparison with the FWHM of the coherence function of the light source, whereby the degradation of the vertical resolution can be suppressed in comparison with the case of using only BK7.

Polycarbonate is easier to change over time than glass. Thus, when polycarbonate is used, a mechanism for controlling the tilt of the optical axis may be provided to compensate for aging and a mechanism for moving in a direction parallel to the optical axis may be provided to change a polycarbonate transmission portion of the reference light. Such a control of the tilt when polycarbonate is used also corresponds to the change in thickness of the dispersion compensation unit along an optical axis of the reference light. Thus, these mechanisms can also be implemented by a unit for changing the thickness of the dispersion compensation unit along an optical axis of the reference light.

The polycarbonate has birefringence, and birefringence index changes due to heat and stress. In recent years, research into reduction of the birefringence of optical polymers is progressing. When optical plastic such as polycarbonate is used in a dispersion compensation member, the birefringence index can be reduced to some extent by devising the molding method. A smaller birefringence index of polycarbonate is desirable. Thus, it is preferable to provide a unit for reducing or suppressing such a birefringence effect of the dispersion compensation unit or to preliminarily reduce the birefringence effect.

Alternatively, a temperature adjustment mechanism may be provided to prevent birefringence due to thermal stress caused by temperature change. Further, in order to reduce strain stress, the front and back of the polycarbonate may be fixed in series along the optical axis by BK7. More specifically, when a plurality of dispersion compensation units includes a dispersion compensation unit made of a material having characteristics such that optical characteristics of the polycarbonate change due to temperature, additional stress, aging, and the like, it is preferable to further include a unit for controlling the conditions of a heater or a pressurizer for controlling the conditions of ambient temperature and added stress. According to the present embodiment, the dispersion compensation unit made of BK7 is located in a position closest to the reflection mirror 107, and thus the unit for controlling the conditions is preferably located in a position corresponding to this position. Note that for example, the optical glass and the BK7 can be reversed in position. In this case, the unit for controlling the conditions is preferably located in a position corresponding to this position.

Second Embodiment

Figure 2:
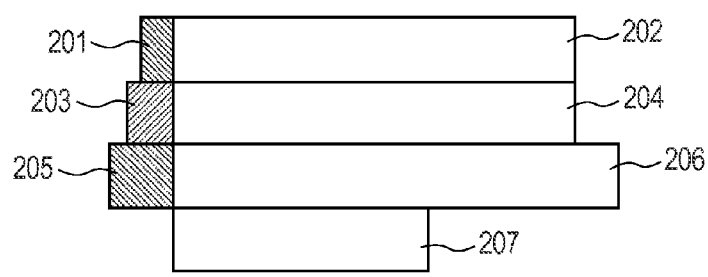
FIG. 2 illustrates a dispersion compensation portion of a second embodiment.

In the present embodiment, a plurality of composite dispersion compensation members including materials 1 and 2 satisfying expression (4) is arranged each having a different thickness as illustrated in FIG. 2.

The present embodiment can provide the dispersion compensation members each suitably compensating for near-sightedness, normal sightedness, or farsightedness. FIG. 2 illustrates dispersion compensation members 201 and 202 for use in measuring an object to be inspected for farsightedness; dispersion compensation members 203 and 204 for normal sightedness with normal axial length; and dispersion compensation members 205 and 206 for nearsightedness. More specifically, the present embodiment uses the conditions listed in the following Table 1.

TABLE 1

| Polycarbonate | Thickness (mm) | BK7 | Thickness (mm) |
|---|---|---|---|
| 201 | 1.7 | 202 | 23 |
| 203 | 2 | 204 | 23 |
| 205 | 2.2 | 206 | 23.7 |

A dispersion compensation member 207 is provided for calibration when a schematic eye or a mirror is placed as the object to be inspected. The axial length can be acquired in advance by measuring the axial length by an axial length measuring instrument before OCT measurement. When BK7 and polycarbonate are used as the materials 1 and 2, if the axial length is about ±1 mm of an assumed axial length as illustrated in FIG. 7, the residual dispersion can be as small as about one-half of the FWHM of the coherence function of the light source. As a result, the resolution degradation can be about 10% which can be considered to be within a range of no problem. Thus, a practical number (three kinds in the Figure) of various axial lengths can be implemented.

Other Embodiments

The present invention can be implemented by executing the following processing. More specifically, the processing is such that software (program) for executing the functions of the above described embodiments is supplied to a system or an apparatus through a network or various storage media; and then, a computer (or a CPU or an MPU) in the system or the apparatus reads and executes the software.

The present invention is not limited to the above embodiments, and various modifications or changes can be made to the present invention without departing from the spirit and scope of the present invention. For example, the above embodiments have described the case in which the object to be measured is an eye, but the present invention can be applied to other objects to be measured such as skin or organ other than eye. In this case, the present invention has an embodiment as medical equipment such as an endoscope other than an ophthalmic apparatus. Thus, it is desirable that the present invention is understood as an inspection apparatus exemplified as an ophthalmic apparatus, and the eye to be inspected is understood as an embodiment of the object to be inspected.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2011-143085, filed Jun. 28, 2011, which is hereby incorporated by reference herein in its entirety.

What is claimed is:

1. An optical coherence tomography apparatus acquiring a tomographic image of an object to be inspected based on an interference light obtained by causing a return light from a measuring light emitted onto the object to be inspected to interfere with a reference light corresponding to the measuring light, said apparatus comprising:
    a first dispersion compensation unit having a first dispersion compensation characteristic in a wavelength band of the measuring light;
    a second dispersion compensation unit provided onto the first dispersion compensation unit and having a second dispersion compensation characteristic in the wavelength band of the measuring light.

2. An optical coherent tomography apparatus according to claim 1, further comprising an image acquiring unit which acquires a tomographic image of the object to be inspected, based on the interference light.

3. An optical coherence tomography apparatus according to claim 1, wherein the first dispersion compensation unit and the second dispersion compensation unit have thicknesses without wavelength dependences of the dispersion characteristics over the wavelength band of the measuring light.

4. The optical coherence tomography apparatus according to claim 1, wherein the first and second dispersion compensation units arranges a pair of dispersion compensation units each having a relation such that differential characteristics about a wavelength of a function expressed by a group velocity dispersion of a dispersive material/the group velocity dispersion of the dispersive material of an object to be measured are reversed in sign.

5. The optical coherence tomography apparatus according to claim 1, wherein the first and the second dispersion compensation units each further includes a unit for changing a thickness along an optical axis of the reference light.

6. The optical coherence tomography apparatus according to claim 1, wherein the first and second dispersion compensation units are arranged by a dispersion compensation unit made of optical glass and a dispersion compensation unit made of optical plastic.

7. The optical coherence tomography apparatus according to claim 6, wherein the optical plastic is polycarbonate.

8. The optical coherence tomography apparatus according to claim 6, wherein a birefringence effect of the optical plastic is reduced.

9. The optical coherence tomography apparatus according to claim 1, further comprising a unit for controlling a condition of at least one dispersion compensation unit of the first and second dispersion compensation units.

* * * * *